United States Patent [19]

Hofstetter et al.

[11] Patent Number: 5,312,392
[45] Date of Patent: May 17, 1994

[54] INTERSTITIAL LASER COAGULATION TREATMENT FOR BENIGN PROSTATIC HYPERPLASIA

[75] Inventors: Alfons Hofstetter, Unterhaching; Rolf Muschter, Starnberg; Stefan Hessel, Munich; Frank Frank, Ebersbert, all of Fed. Rep. of Germany

[73] Assignee: Messerschmitt-Boelkow-Blohm AG, Fed. Rep. of Germany

[21] Appl. No.: 936,408

[22] Filed: Aug. 31, 1992

[51] Int. Cl.$^5$ .............................. A61B 17/36
[52] U.S. Cl. ............................. 606/2; 606/3; 606/15; 606/16
[58] Field of Search ............... 128/898, 395, 397, 398; 606/15, 14, 2, 3

[56] References Cited

U.S. PATENT DOCUMENTS

| | | | |
|---|---|---|---|
| 4,336,809 | 6/1982 | Clark | 128/395 |
| 4,760,840 | 8/1988 | Fournier, Jr. et al. | 606/15 |
| 4,762,128 | 8/1988 | Rosenbluth | 606/192 |
| 4,878,725 | 11/1989 | Hessel et al. | 350/96.15 |
| 4,950,267 | 8/1990 | Ishihara et al. | 606/15 |
| 5,061,266 | 10/1991 | Hakky | 606/15 |
| 5,074,867 | 12/1991 | Wilk | 606/128 |
| 5,159,925 | 11/1992 | Neuwirth et al. | 606/28 |

OTHER PUBLICATIONS

Hi-Tech of the Prostate, R. Muschter, A. Hofstetter, S. Hessel, E. Keiditsch, K. Rothenberger, P. Schneede.
Die Interstitielle Laserkoagulation der Benignen Prostatahyperplasie, R. Muschter, S. Hessel, A. Hofstetter, E. Keiditsch, K.-H. Rothenberger, P. Schneede, F. Frank.
Erste Erfahrungen mit Dem Einsatz Des ND: Yag Lasers Bei der Behandlung Des Prostatakarzinoms, S. Sander.
Indikationen und Indikations-Grenzen für Den Nd: Yag Laser Bei Gastrointestinalen Blutungen, R. Sander.
Interstitielle Thermokoagulation (ITK) Von Prostatatumoren, A. Hofstetter.
Interstitial Laser Coagulation in Benign Prostatic Hyperplasia, R. Muschter et al.

Primary Examiner—Stephen C. Pellegrino
Assistant Examiner—Sonya Harris
Attorney, Agent, or Firm—Evenson, McKeown, Edwards & Lenahan

[57] ABSTRACT

A method of treating benign prostatic hyperplasia employs the steps of inserting a diffusing light guide into a prostrate lobe and providing laser power to the diffusing light guide in order to necrose surrounding tissue. The diffusing light guide can be inserted into the central or lateral prostrate lobes by inserting a needle and a trocar transperineally into the middle of the lateral lobe, removing the trocar, inserting the diffusing light guide, and monitoring the position of the needle, trocar, and diffusing light guide using ultrasound. The diffusing light guide can also be inserted into the central or lateral prostrate lobes transurethrally and positioned with the aid of an urethroscope.

13 Claims, 3 Drawing Sheets

20mm

INTERSTITIAL LASER COAGULATION TREATMENT FOR BENIGN PROSTATIC HYPERPLASIA

BACKGROUND AND SUMMARY OF THE INVENTION

This invention relates to the field of treating benign prostatic hyperplasia and more particularly to the field of treating benign prostatic hyperplasia with laser energy.

Open surgery and transurethral resection are increasingly reliable and safe procedures for treating benign prostatic hyperplasia (BPH). The trend towards minimally invasive modes of therapy, however, can also be observed with respect to BPH. One reason is that as life expectancy grows, there is a greater number of aged patients who reach the stage where they require treatment, some of them suffering from BPH in addition to other conditions. Secondly, a large number of patients are simply afraid of surgical intervention and the possibility of complications. This is proven not only by the widespread use of phytopharmacological preparations, but also by the fact that new therapeutic approaches tend to become quickly popular, for example hyperthermia.

The current literature reports on a multitude of rediscovered and novel treatment concepts, which include various pharmacological methods, balloon dilatation, intraprostatic stents, focussed ultrasound therapy and cryosurgery, as well as different systems of hyperthermia and thermotherapy, where microwaves, for example, are applied transrectally or transurethrally.

Several work groups have been working with transurethral laser applications. Interstitial application, although arguably a logical next step, has so far been problematic: the customarily used bare fibers or contact tips led to a high concentration of heat, which resulted in uncontrollable carbonization, a process that absorbs laser rays and consequently prevents deep coagulation of the tissues.

It is known that an Nd:YAG laser (such as the Medilas 4060N fiberTome TM, MBB Medizintechnik GmbH, Munich, Germany and Sharplan 3000 laser from Laser Industries Ltd., Tel Aviv, Israel) produces deep tissue coagulation in a minimally invasive manner, produces favorable coagulation properties, and has the ability to deliver radiation through light guides. However, in order to avoid carbonization of tissue, the power density must not exceed a value of between 5-10 Watts per square cm.

The power at the end of a bare light guide can be dispersed by employing the apparatus disclosed in U.S. Pat. No. 4,878,725 to Hessel et. al. titled "Apparatus for the Circumferential Irradiation of Objects". Hessel et. al. shows a diffusing light guide having a clear glass cap placed at the end of a fiber for diffusing light transmitted through the fiber. However, Hessel does not disclose how to use the diffusing light guide for treating BHP.

An object of the invention is to provide improved treatment arrangement and process for treating benign prostatic hyperplasia.

According to the present invention, a diffusing light guide into a prostate lobe and providing laser method of treating benign prostatic hyperplasia comprises the steps of inserting a power to the diffusing light guide in order to necrose and shrink surrounding tissue.

In exemplary preferred embodiments of the invention, the diffusing light guide is inserted into the central or lateral prostate lobes by inserting a trocar needle and a trocar sheath transperineally into the lobe, removing the trocar needle, inserting the diffusing light guide into the trocar sheath, and monitoring the position of the trocar needle, trocar sheath, and diffusing light guide using ultrasound.

In exemplary preferred embodiments of the invention, the diffusing light guide is inserted into the central or lateral prostate lobes transuretherally and positioned with the aid of an urethroscope.

In exemplary preferred embodiments of the invention, the diffusing light guide is an ITT (interstitial thermal therapy) light guide having a cap with a diameter between 1 and 3 mm and a length of between 10 to 30 mm.

In exemplary preferred embodiments of the invention, the diffusing light guide has cap with a diameter of 1.9 mm and a length and an active length of 20 mm and 15 mm, respectively.

Using the diffusing light guide to necrose prostrate tissue eliminates the need for surgical treatment and for the other treatments discussed above. Using a diffusing light guide instead of a bare light guide eliminates the carbonization problem associated with bare light guides.

Other advantages and novel features of the present invention will become apparent from the following detailed description of the invention when considered in conjunction with the accompanying drawings.

DESCRIPTION OF THE PREFERRED EMBODIMENTS

Figure 1:
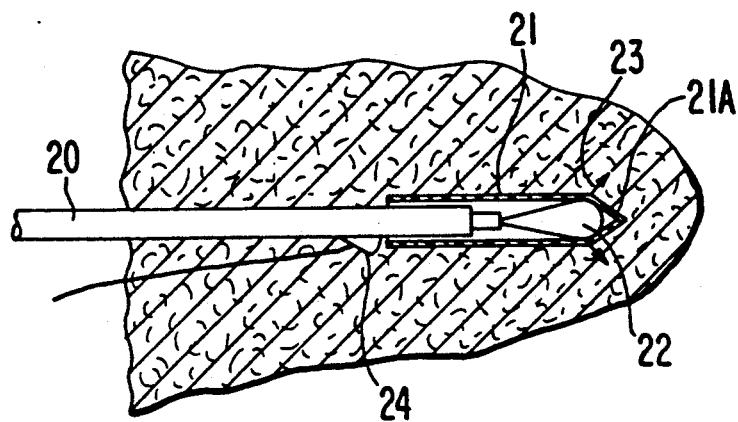
FIG. 1 shows a diffusing light guide used in an exemplary embodiment of the present invention.

Referring to FIG. 1, a diffusing light guide 21 is connected to an Nd:YAG laser (not shown) and produces a diffuse light beam 22 that provides power, in the form of heat, to surrounding prostate tissue 23. The diffusing light guide 20 can be an ITT (interstitial thermal therapy) light guide available commercially from MBB Medizintechnik GmbH and shown in U.S. Pat. No. 4,878,725 to Hessel et. al. titled "Apparatus for the Circumferential Irradiation of Objects", which is hereby incorporated by reference. The ITT light guide has a cap 21 with a needle shaped tip 21a and has a diameter between 1 and 3 mm and a length of between 10 and 30 mm. An exemplary embodiment of the invention uses an ITT light guide having a 1.9 mm diameter cap and a length of 20 mm (15 mm active length). However, it will be appreciated by one skilled in the art that other types of diffusing light guides could also be used.

The laser can be any one of a plurality of standard, commercially available lasers, such as the Nd:YAG lasers enumerated above or can be any other appropriate type of laser.

In the case of the central prostate lobe, the diffusing light guide 20 is inserted transurethrally. A urethroscope is used to visually place the diffusing light guide. If necessary, a urethrotomia is performed. Inserting the diffusing light guide 20 into the lateral lobes is performed by inserting a trocar needle and a trocar sheath transperineally. The trocar needle is inserted in the middle of the lateral lobe, the trocar needle removed, the diffusing light guide 20, having a trocar sheath thereon, is pushed forward of the trocar sheath, and the sheath trocar is removed. The positions of the trocar needle, trocar sheath, and diffusing light guide 20 are monitored using ultrasound. The patient is put under general anesthesia for this procedure, although it would be possible to perform the procedure using only local anesthesia. Note that it is also possible to insert the light guide 20 transuretherally into the lateral lobes or transperineally into the central lobe.

Figure 2:
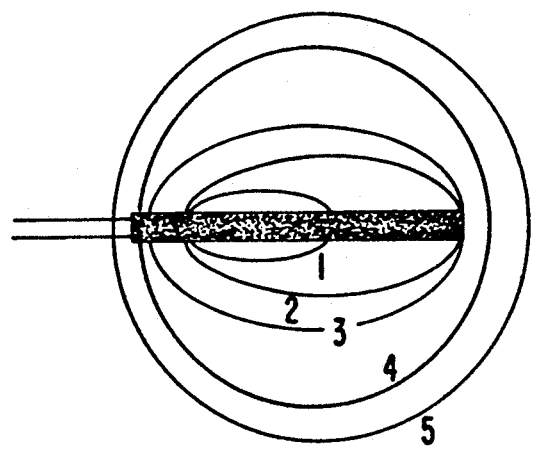
FIG. 2 graphically illustrates the time-dependant size of areas of tissue necrosed by a diffusing light guide.

After the diffusing light guide 20 is inserted, the laser provides power to the light guide 20. Heat from the diffuse light beam 22 necroses surrounding prostate tissue. During the process, temperature can be measured by a probe 24 in the surrounding tissue 23. By way of analogy, FIG. 2 graphically illustrates the size and shape of areas necrosed as a function of time for pork liver tissue, which has been found to have similar properties to human prostate tissue. It can be noted from FIG. 2 that, as expected, the area that is necrosed increases as a function of time.

Figure 3:
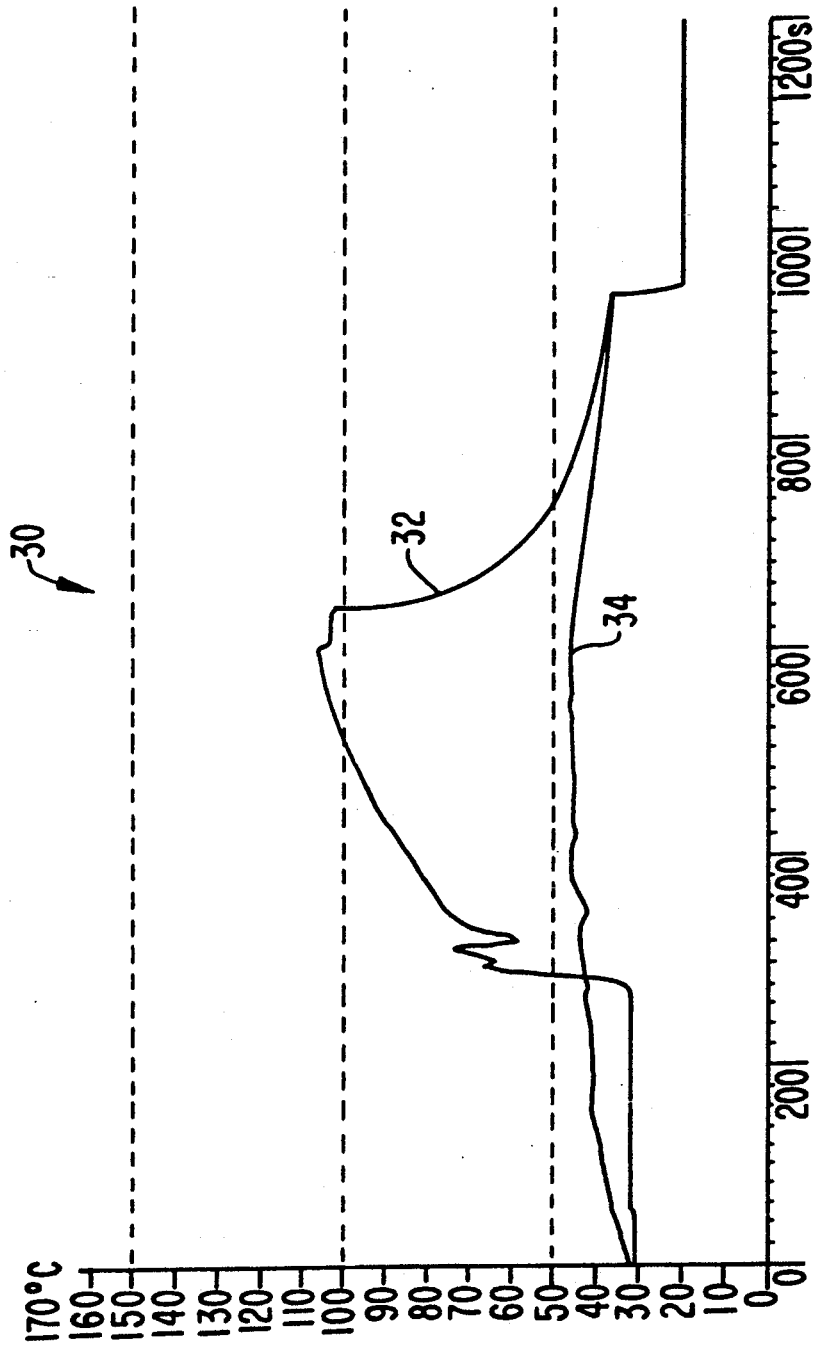
FIG. 3 is a graph illustrating temperature of tissue as a function of time for two distances from a diffusing light guide.

For the diffusing light guide 20 that has been inserted into the prostate, the laser provides between 3 to 20 Watts of power for 5 to 20 minutes to the light guide 20, although in certain preferred embodiments, five Watts of power for ten minutes is used. FIG. 3 is a graph 30 having a horizontal axis indicative of time and a vertical axis indicative of temperature. A first plot 32 and a second plot 34 indicate temperature of surrounding tissue as a function of time. The first plot 32 is for a sensor placed relatively close to the end of the diffusing light guide 21 and the second plot 34 is for a sensor placed farther away from the diffusing light guide 21.

In clinical studies of the method discussed above, it was found that the necrosing prostate tissue with the diffusing light guide causes the prostate to shrink without causing damage to nearby organs.

Figure 4B:
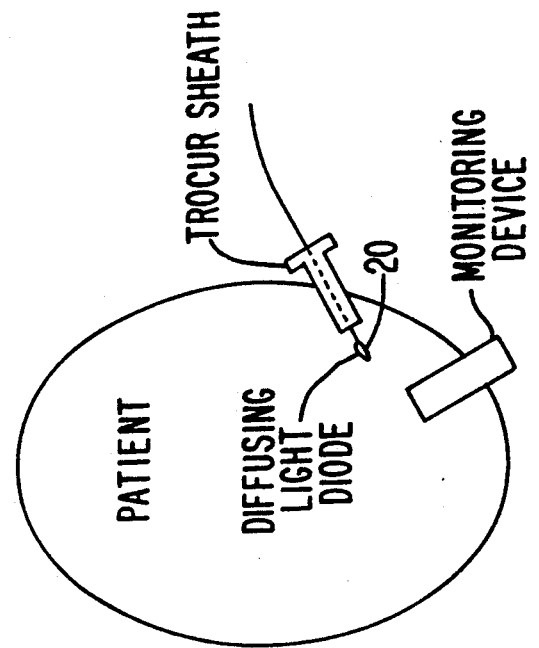
FIG. 4b is a schematic illustration showing use of the trocar sheath, diffusing light guide and a monitoring device on a patient.
Figure 4A:
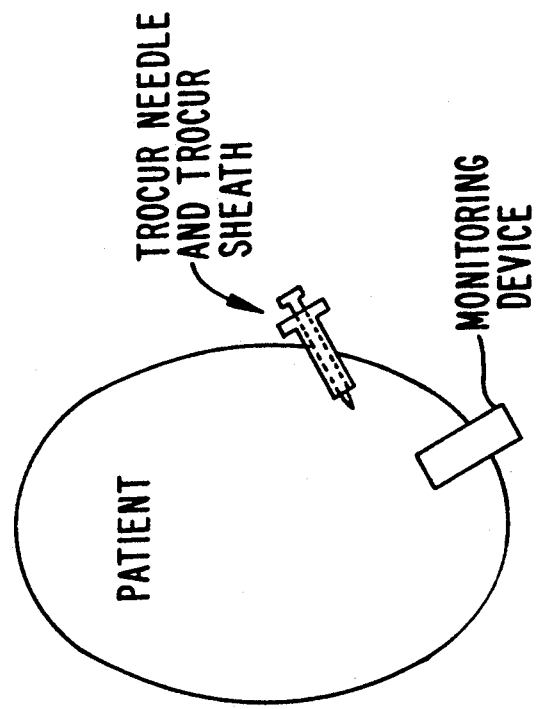
FIG. 4a is schematic illustration showing use of a trocar needle, trocar sheath and a monitoring device on a patient.

Referring to FIG. 4a, a monitoring device, such as urethroscope or an ultrasound monitoring device, is used on a patient to monitor a position of a trocar needle and a trocar sheath inserted into the patient. The monitoring device can be any type of monitoring device, known to one of the ordinary skill in the art, suitable for monitoring the position of the trocar needle and the trocar sheath. During insertion of the trocar needle and trocar sheath, the monitoring device is used to observe the position thereof and to ensure that the trocar needle and trocar sheath are correctly inserted into the proper area.

Referring to FIG. 4b, a trocar needle has been removed from the trocar sheath and the diffusing light guide 20 has been inserted into the patient through the trocar sheath. The monitoring device can be used both during insertion of the diffusing light guide and when the diffusing light guide is placed forward of the trocar sheath. The monitoring device ensures proper placement of the diffusing light guide.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed is:

1. A method of treating benign prostatic hyperplasia, comprising the steps of:
    inserting a diffusing light guide into a prostate lobe; and
    providing laser power to the diffusing light guide in order to necrose surrounding tissue.

2. A method of treating benign prostatic hyperplasia, according to claim 1, wherein the step of inserting includes inserting the diffusing light guide into one of a central and a lateral prostate lobe by the steps of:
    inserting a trocar needle and a trocar sheath transperineally into one of the central and the lateral lobe;
    removing the trocar needle;
    inserting the diffusing light guide in the trocar sheath; and
    monitoring the position of the trocar needle, trocar sheath, and diffusing light guide using ultrasound.

3. A method of treating benign prostatic hyperplasia, according to claim 1, wherein the step of inserting includes inserting the diffusing light guide transurethrally into one of a central and lateral prostate lobe and positioning the diffusing light guide with the aid of an urethroscope.

4. A method of treating benign prostatic hyperplasia, according to claim 1, wherein the step of inserting a diffusing light guide includes inserting an ITT (interstitial thermal therapy) light guide to a depth sufficient for an ITT light guide having a cap with a diameter between 1 and 3 mm and a length of between 10 to 30 mm.

5. A method of treating benign prostatic hyperplasia, according to claim 4, wherein the step of inserting the diffusing light guide includes inserting the light guide to a depth sufficient for an ITT light guide having a cap with a diameter of 1.9 mm and an overall length of 20 mm and an active length, for irradiating light, of 15 mm.

6. A method of treating benign prostatic hyperplasia, according to claim 1, wherein the step of providing laser power includes providing between 3 to 20 Watts of power to the diffusing light guide for 5 to 20 minutes.

7. A method of treating benign prostatic hyperplasia according to claim 6, wherein the step of providing laser power includes providing five Watts of power to the diffusing light guide for ten minutes.

8. A method of treating benign prostatic hyperplasia, according to claim 2, wherein the step of inserting a diffusing light guide includes inserting an ITT (interstitial thermal therapy) light guide to a depth sufficient for an ITT light guide having a cap with a diameter between 1 and 3 mm and a length of between 10 to 30 mm.

9. A method of treating benign prostatic hyperplasia, according to claim 8, wherein the step of inserting diffusing light guide includes inserting the light guide to a depth sufficient for an ITT light guide having a cap with a diameter of 1.9 mm and an overall length and of 20 mm and an active, for irradiating light, of 15 mm.

10. A method of treating benign prostatic hyperplasia, according to claim 9, wherein the step of providing laser power includes providing between 3 to 20 Watts of power to the diffusing light guide for 5 to 20 minutes.

11. A method of treating benign prostatic hyperplasia, according to claim 10, wherein the step of providing laser power includes providing five Watts of power to the diffusing light guide for ten minutes.

12. A method of treating benign prostatic hyperplasia, according to claim 1, wherein the step of inserting the diffusing light guide includes inserting the light guide in a manner sufficient for a light guide having a cap with a needle shaped tip for one of transperineally and transurethrally inserting the cap into one of a central and lateral prostate lobe.

13. A method of treating benign prostatic hyperplasia, according to claim 1, further including the step of inserting a temperature probe into a prostate lobe for measuring the temperature within the prostate lobe while power is being applied to the diffusing light guide.

* * * * *

Adverse Decisions In Interference

Patent No. 5,312,392, Alfons Hofstetter, Rolf Muschter, Stefan Hessel, Frank Frank, INTERSTITIAL LASER COAGULATION TREATMENT FOR BENIGN PROSTATIC HYPERPLASIA, Interference No. 103,871, final judgment adverse to the patentees rendered December 17, 1997, as to claims 1 and 13.

*(Official Gazette June 2, 1998)*